United States Patent
Kumar et al.

(10) Patent No.: US 11,628,137 B2
(45) Date of Patent: Apr. 18, 2023

(54) PARENTERAL FORMULATION COMPRISING SIPONIMOD

(71) Applicant: Novartis AG, Basel (CH)

(72) Inventors: Rajesh Kumar, Raidurg (IN); Mandala Rayabandla Sunil Kumar, Raidurg (IN); Henricus Lambertus Gerardus Maria Tiemessen, Basel (CH)

(73) Assignee: NOVARTIS AG, Basel (CH)

( * ) Notice: Subject to any disclaimer, the term of this patent is extended or adjusted under 35 U.S.C. 154(b) by 131 days.

(21) Appl. No.: 16/650,803

(22) PCT Filed: Sep. 26, 2018

(86) PCT No.: PCT/IB2018/057425
§ 371 (c)(1),
(2) Date: Mar. 25, 2020

(87) PCT Pub. No.: WO2019/064185
PCT Pub. Date: Apr. 4, 2019

(65) Prior Publication Data
US 2020/0230049 A1    Jul. 23, 2020

(30) Foreign Application Priority Data
Sep. 27, 2017 (IN) .............................. 201711034371

(51) Int. Cl.
| | |
|---|---|
| *A61K 9/00* | (2006.01) |
| *A61K 31/397* | (2006.01) |
| *A61K 31/724* | (2006.01) |
| *A61K 31/047* | (2006.01) |
| *A61K 47/18* | (2017.01) |

(52) U.S. Cl.
CPC .......... *A61K 9/0019* (2013.01); *A61K 31/397* (2013.01); *A61K 31/724* (2013.01); *A61K 31/047* (2013.01); *A61K 47/18* (2013.01)

(58) Field of Classification Search
CPC ................ A61K 31/047; A61K 31/397; A61K 31/724; A61K 47/18; A61K 47/26; A61K 47/40; A61K 9/0019; A61K 9/08
See application file for complete search history.

(56) References Cited

U.S. PATENT DOCUMENTS 7,855,193 B2    12/2010  Saha et al.
2012/0115840 A1*  5/2012  Ciszewski ............ A61K 31/397
                                                      514/210.17

FOREIGN PATENT DOCUMENTS

| JP | A-2007-513925 | 5/2007 |
| WO | WO 2004/103306 | 12/2004 |
| WO | WO 2005/58346 | 6/2005 |
| WO | WO 2015/155711 | 10/2015 |
| WO | WO 2017/067980 | 4/2017 |

OTHER PUBLICATIONS

Loftsson et al. (Journal of Pharmaceutical sciences, vol. 101, No. 9, 2012, pp. 3019-3032 (Year: 2012).*
Mehmood (Open science journal of pharmacy and pharmacology, 2015, 3 (3): 19-27) (Year: 2015).*
Brewster, M.E. et al., "The Potential use of Cyclodextrins in Parenteral Formulations," Journal of Parenteral Science and Technology, 1989, 43(5), pp. 231-240.
Gentile A. et al., "Siponimod (BAF312) prevents synaptic neurodegeneration in experimental multiple sclerosis," Journal of Neuroinflammation, 2016, 13:207. (13 pages).
Li W. et al., "Quantitative determination of BAF312, a S1P-R modulator, in human urine by LC-MS/MS: Prevention and recovery of lost analyte due to container surface adsorption," Journal of Chromatography B, 82010, 78(5-6), pp. 583-589.
Szejtli J. "Dimethyl-Beta-Cyclodextrin as Parenteral Drug Carrier," Journal of Inclusion Phenomena, 1, 1983, pp. 135-150.
Uekama K. "Pharmaceutical Application of Cyclodextrins as Multi-Functional Drug Carriers," Yakugaku Zasshi, 2004, vol. 124, No. 24, pp. 909-935.

* cited by examiner

*Primary Examiner* — Savitha M Rao

(74) *Attorney, Agent, or Firm* — Finnegan, Henderson, Farabow, Garrett & Dunner, LLP

(57) ABSTRACT

The present invention relates to a pharmaceutical formulation of siponimod which can be administered parenterally. In particular, the present invention relates to a parenteral solution comprising siponimod and a method for preparing said solution.

17 Claims, 1 Drawing Sheet

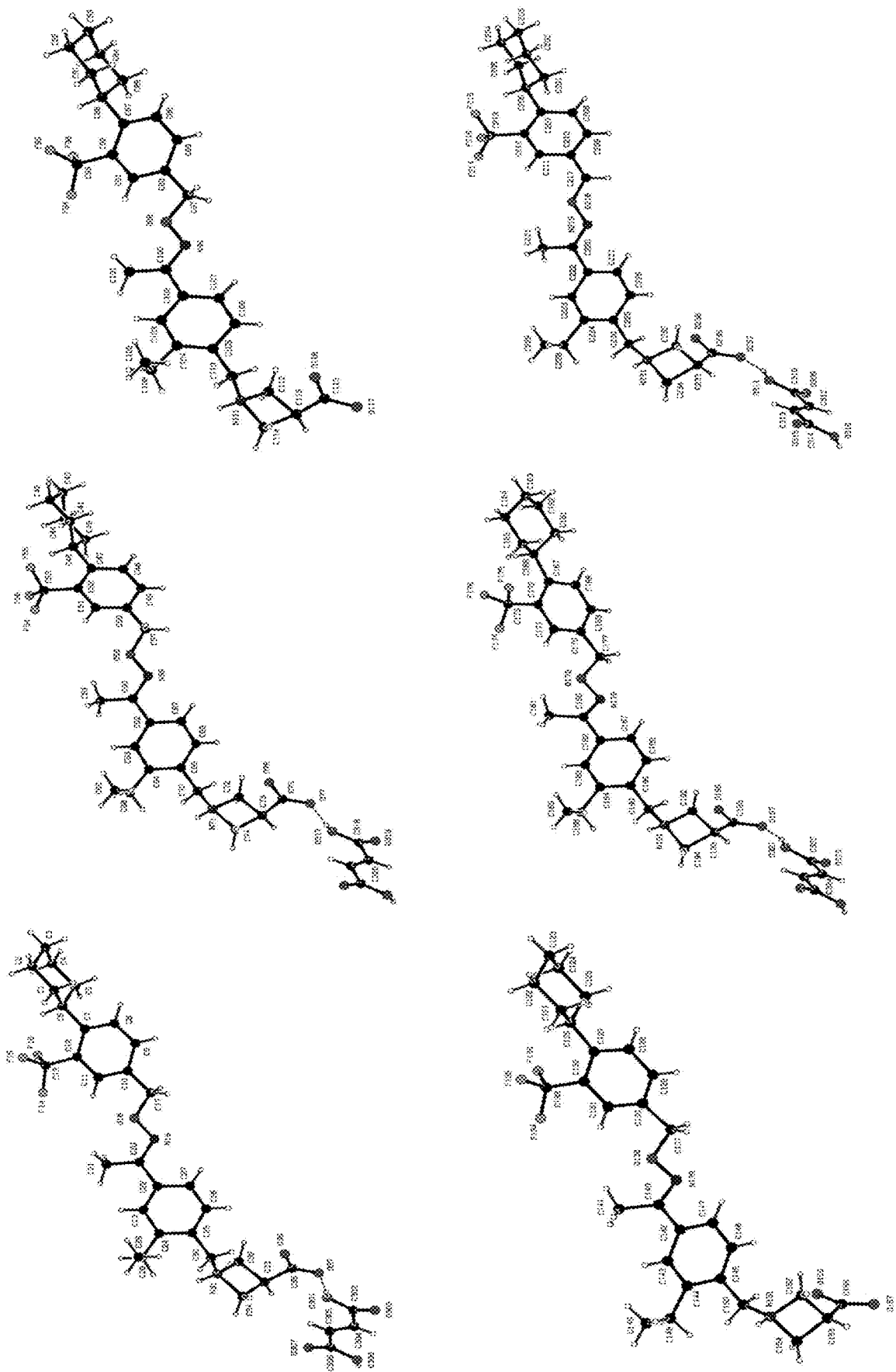

PARENTERAL FORMULATION COMPRISING SIPONIMOD

RELATED APPLICATIONS

This application is a U.S. National Phase filing of International Application Serial No. PCT/IB2018/057425 filed 26 Sep. 2018 and claims priority to Indian Provisional Application Serial No. 201711034371 filed 27 Sep. 2017 all of which are incorporated in their entireties herein.

The present invention relates to a pharmaceutical formulation of siponimod which can be administered parenterally. In particular, the present invention relates to a parenteral solution comprising siponimod and a method for preparing said solution.

BACKGROUND OF THE INVENTION

The IUPAC name of siponimod is 1-{4-[(1E)-N-{[4-cyclohexyl-3-(trifluoromethyl)benzyl]oxy}ethanimidoyl]-2-ethylbenzyl}-3-azetidinecarboxylic acid and the compound is represented by the chemical structure according to Formula (I):

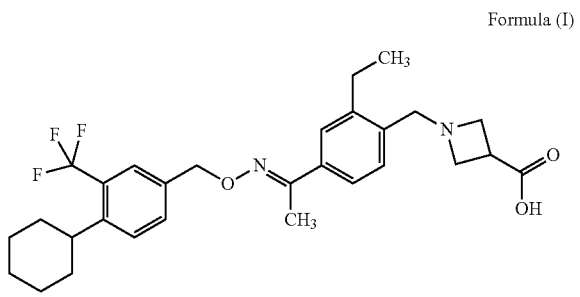 [SMILES: CCc1cc(/C(C)=N/OCc2ccc(C3CCCCC3)c(C(F)(F)F)c2)ccc1CN1CC(C(=O)O)C1]

Formula (I)

Siponimod (also referred to as BAF312) is a selective sphingosine-1-phosphate receptor modulator which is used in the treatment of autoimmune diseases, such multiple sclerosis (MS), in the treatment of neurodegenerative diseases.

WO 2004/103306 A2 relates to immunosuppressant compounds and processes for their production. Inter alia, a synthesis pathway for siponimod is described. Further, said document mentions that siponimod can generally be administered by any conventional administration route such as enterally, parentally, topically and in nasal or suppository form. However, said document does not describe any specific dosage form.

Oral dosage forms of siponimod are known in the art. Tablets containing siponimod, for example, are described in WO 2012/093161 A1 and WO 2015/155711 A1. Further, WO 2007/021666 A2 relates to oral liquids of S1P-receptor agonists.

Taking into account the variety of indications of siponimod, there is a need for further ways of administration of the active pharmaceutical ingredient.

In view of this, the applicant conducted internal experiments with regard to a lyophilized composition which is reconstituted and optionally further diluted with e.g. saline or 5% glucose (=dextrose) solution to provide infusion solutions. For this purpose, formulations containing a lyophilisate comprising siponimod and parenteral grade excipients such as common cryoprotectants were tested. It turned out that trehalose stabilized the lyophilisate better than sucrose/lactose and mannitol. Nevertheless, the lyophilized formulation had a shelf life of about 12 months when stored under normal freezing conditions; i.e. in a freezer at a temperature of −15° to −20° C. Due to this stability limitation, the corresponding lyophilized formulation was considered to be not sufficiently suitable for long-term clinical studies. However, in view of the above-mentioned medical indications of siponimod, such long-term studies as well as administrations were essential.

Thus, there is still a need of stable formulations/dosage forms of siponimod which are not administered orally. In particular, a parenteral formulation having the required properties suitable for a long-term clinical study, such as storage stability, is still needed.

Hence, it was an object of the present invention to overcome the above drawbacks.

Thus, it was an object of the present invention to provide further dosage forms comprising siponimod which are not administered orally. Moreover, it was an object to provide further dosage forms comprising siponimod which are suitable for long-term clinical studies as well as long-term administration. In view of that, dosage forms, in particular stable dosage forms comprising siponimod, should be provided.

Further, it was an object of the present invention to provide a composition of siponimod which is suitable for parenteral administration, wherein the active ingredient is rather highly concentrated but stable in liquid form.

SUMMARY OF THE INVENTION

The above problems are overcome in view of the subject-matter of the present invention. The present invention provides a parenteral formulation comprising (A) siponimod, (B) cyclodextrin, (C) buffer agent and (D) solvent and optionally (E) a tonicity agent. This parenteral formulation can be in liquid form and, thus, suitable for intravenous administration (also referred to as i.v. administration), such as injections or infusions.

Moreover, the present invention provides to a method for preparing the present parenteral formulation comprising the steps of:
(i) providing (A) siponimod, (B) cyclodextrin, (C) buffer agent and (D) solvent, optionally (E) a tonicity agent and optionally one or more pharmaceutically acceptable excipient(s),
(ii) mixing the components of steps (i) to form a solution
(iii) filtering the solution of step (ii).

BRIEF DESCRIPTION OF THE FIGURE

FIG. 1. ORTEP representations of siponimod-fumaric acid co-crystal showing the 4 four (O—H . . . O) pairs.

DETAILED DESCRIPTION OF THE INVENTION

Throughout the description and claims of this specification, the words "comprise" and "contain" and variations of them mean "including but not limited to" and they are not intended to (and do not) exclude other moieties, additives, components, integers or steps.

Throughout the description and claims of this specification, the singular encompasses the plural unless the context otherwise requires. In particular, where the indefinite article is used, the specification (which term encompasses both the description and the claims) is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings) and/or all of the steps of any method or process so disclosed may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "treatment" includes: (1) preventing or delaying the appearance of clinical symptoms of the state, disorder or condition developing in an animal, particularly a mammal and especially a human that may be afflicted with or predisposed to the state, disorder or condition but does not yet experience or display clinical or subclinical symptoms of the state, disorder or condition; (2) inhibiting the state, disorder or condition (e.g. arresting, reducing or delaying the development of the disease or a relapse thereof in case of maintenance treatment, of at least one clinical or subclinical symptom thereof); and/or (3) relieving the condition (i.e. causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

Generally, a parenteral formulation can be regarded as a formulation which is administered by bypassing the gastrointestinal tract. Reference is made to Ph.Eur. 8.0, section "Parenteralia". In a preferred embodiment the formulation of the present invention is administered by infusion or injection. In particular, the formulation of the present invention is administered intravenously.

In a preferred embodiment the parenteral formulation of the present invention is present in liquid form. Preferably, the parenteral formulation of the present invention is a solution. Suspensions are less preferred.

In a preferred embodiment the parenteral formulation of the present invention can be in form of a concentrate.

Within this application a "concentrate" is referred to as a parenteral formulation which preferably is not administered directly to a patient but diluted before administration. For example, the concentrate can be diluted with a suitable liquid, e.g. with 5% glucose solutions or saline, to give a ready-for-use-formulation, which e.g. can be administered as infusion or injection. Alternatively (but less preferred) the concentrate may be used to be administered directly. Generally, in the art concentrates are also referred to as "Parenteralia diluenda".

In an alternative preferred embodiment the parenteral formulation can be a "ready-to use" formulation. The term "ready-to-use" in the context of the present invention typically means that no further preparation step is necessary before administering the parenteral formulation to the patient, for example by injecting the formulation. Moreover, there is no need to add further additives or solvents, such as water, for injection before administration of the parenteral formulation.

In an alternative embodiment the parenteral formulation can be further processed to the desired dosage form, such as an infusion. For preparing an infusion, the parenteral solution can by combined with further additives and solvents, in particular water, for injection. Such an infusion solution may subsequently be administered to a patient via a drip.

Generally, pharmaceutical formulations are expected having certain stability. In a preferred embodiment to formulation of the present invention is a stable parenteral formulation. More preferably, the formulation of the present invention has a shelf-life of at least 15 months, still more preferably of at least 20 months, more particular of at least 24 months, when stored at a temperature of between 2 and 8° C.

The parenteral formulation according to the present invention comprises compounds (A) to (D). The compound (A) comprised in the formulation of the present invention is the active pharmaceutical ingredient siponimod.

In the context of this invention, the term "siponimod" refers to (is 1-{4-[(1E)-N-{[4-cyclohexyl-3-(trifluoromethyl)benzyl]oxy}ethanimidoyl]-2-ethylbenzyl}-3-azetidinecarboxylic acid in accordance with Formula (I) above. In addition, the term "siponimod" as used in the present application can refer to siponimod in free form as well as to its pharmaceutically acceptable salts, hydrates, solvates, polymorphs, co-crystals and/or mixtures thereof.

In a preferred embodiment siponimod is added to the formulation in form of an acid addition product, such as a salt or a co-crystal.

The pharmaceutically acceptable salts can e.g. be obtained by the reaction of siponimod with an acid. Examples of pharmaceutically acceptable salts of the compound of siponimod include salts with inorganic acids, such as hydrochloride, hydrobromide and sulfate, as well as salts with organic acids such as acetic acid, maleic acid, benzoic acid, citric acid, malic acid, as well as salts with sulfonic acid, such as methanesulfonic acid or benzenesulfonic acid, or, when appropriate, salts with metals, such as sodium, potassium, calcium and aluminium, salts with amines, such as trimethylamine, and salts with dibasic amino acids, such as lysine.

The compounds and salts of the combination of the present invention encompass hydrate and solvate forms.

In a preferred embodiment siponimod is added to the formulation in form of an acid addition product with fumaric acid.

In a more preferred embodiment siponimod is added to the formulation in form of a co-crystal.

Generally, a cocrystal can be referred to as crystalline material composed of two or more different molecules in the same lattice, wherein these two or more molecules are nonvolatile. Co-crystals can be preferably be distinguished from salts because unlike salts their components are in a neutral state and interact non-ionically.

In a particular preferred embodiment siponimod (A) is added to the formulation as a co-crystal of siponimod with fumaric acid, hereinafter also referred to as (1-{4-[(1E)-N-{[4-cyclohexyl-3-(trifluoromethyl)benzyl] oxy}ethanimidoyl]-2-ethylbenzyl}-3-azetidinecarboxylic acid-fumaric acid co-crystal. The ratio of fumaric acid to 1-{4-[(1E)-N-{[4-cyclohexyl-3-(trifluoromethyl)benzyl]
oxy}ethanimidoyl]-2-ethylbenzyl}-3-azetidinecarboxylic
acid can e.g range from 0.3 to 0.7, preferably be about 0.5.
The IUPAC name of the preferred co-crystal of siponimod
with fumaric acid of the present invention is (2E)-But-2-
enedioic acid-1-({4-[(1E)-N-{[4-cyclohexyl-3(trifluorom-
ethyl)phenyl]methoxy}ethanimidoyl]-2-
ethylphenyl}methyl)azetidine-3-carboxylic acid (½).

In a still more preferred embodiment siponimod is used as
1-{4-[(1E)-N-{[4-cyclohexyl-3-(trifluoromethyl)benzyl]
oxy}ethanimidoyl]-2-ethylbenzyl}-3-azetidinecarboxylic
acid-fumaric acid co-crystal in polymorphic form A having
an X-ray powder diffraction pattern with specific peaks at
6.9, 10.1, 10.6, 12.1, 17.5 18.1 and 20.7° (2θ).

In an alternatively preferred embodiment of the present
invention siponimod is used in the free form. Unless other-
wise mentioned within the present application the amounts
or weight-% of siponimod are based on the amount of
siponimod in free form. That is, if siponimod is present in
form of a salt, the amount of the free from has to be
calculated accordingly. For example, if siponimod is present
in the form of its HCl salt in an amount of 1.00 g, this
amount corresponds to circa 0.93 of free siponimod.

In a further embodiment of the invention, the parenteral
formulation of the present invention can comprise further
APIs, preferably APIs suitable to enhance the effect of the
parenteral formulation. Further APIs may comprise other
drugs, e.g. immunosuppressant(s), steroids(s), such as pred-
nisolone, methylprednisolone dexamethasone, hydrocorti-
sone and the like, or nonsteroidal anti-inflammatory
agent(s). The dosage of a combination treatment may
depend on the effectiveness and site of action of each active
agent as well as synergistic effects between the agents used
for combination therapy.

In an alternative preferred embodiment siponimod is used
as the sole active pharmaceutical ingredient in the formu-
lation and/or the treatment according to the present inven-
tion.

The parenteral formulation of the present invention pref-
erably contains siponimod in a concentration of 0.05 to 3.5
mg/mL, preferably 0.1 to 2.0 mg/mL, more preferably 0.015
to 1.5 mg/mL. In a particularly preferred embodiment the
parenteral formulation being present in form of a concen-
trate can contain siponimod in concentrations of 0.25
mg/mL, 0.5 mg/mL or 1.0 mg/mL, especially 1 mg/mL.

As far as the before-described concentration of siponimod
is concerned, this applies to a parenteral formulation being
present as a concentrate; i.e. in not further diluted form. It is
evident that the concentration gets smaller, if the concentrate
is further diluted for example to form an infusion solution.

Further, the parenteral formulation according to the pres-
ent invention comprises (B) cyclodextrin.

In the present application the term "cyclodextrin" refers to
non-reducing cyclic oligosaccharides and mixtures thereof.
Preferably, said cyclic saccharides comprise six, seven, eight
or nine glucose units, linked by alpha-1,4 interglycosidic
bonds.

A ring-shaped molecule made up of six glucose units and
linked by alpha-1,4 bonds can be referred to as α-cyclodex-
trin, which is represented by Formula (II):

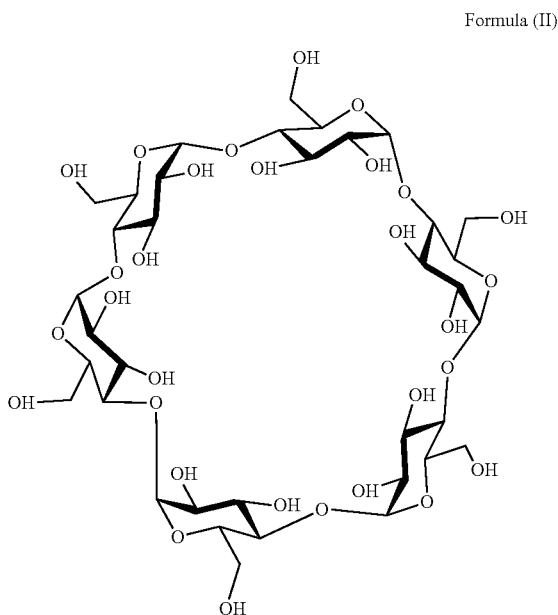 [SMILES: OCC1O[C@@H]2O[C@@H]3C(CO)O[C@H](O[C@@H]4C(CO)O[C@H](O[C@@H]5C(CO)O[C@H](O[C@@H]6C(CO)O[C@H](O[C@@H]7C(CO)O[C@H](O[C@H]1[C@H](O)C2O)C(O)[C@H]7O)C(O)[C@H]6O)C(O)[C@H]5O)C(O)[C@H]4O)C(O)[C@H]3O]

Formula (II)

A ring-shaped molecule made up of seven glucose units
and linked by alpha-1,4 bonds can be referred to as β-cy-
clodextrin, which is represented by Formula (III):

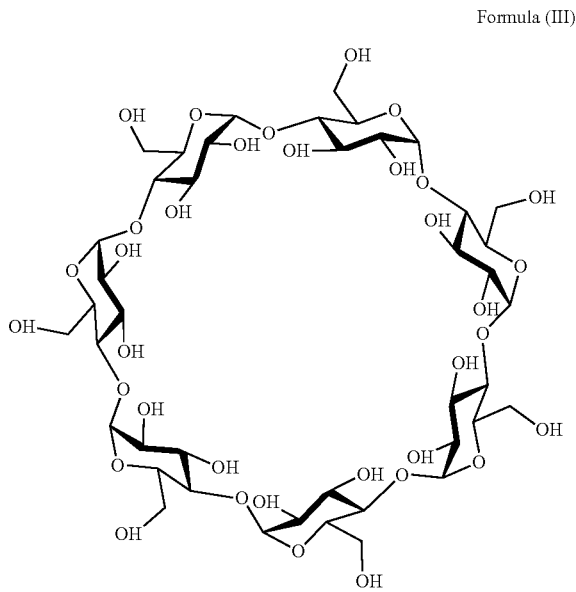 [SMILES: OCC1O[C@@H]2O[C@@H]3C(CO)O[C@H](O[C@@H]4C(CO)O[C@H](O[C@@H]5C(CO)O[C@H](O[C@@H]6C(CO)O[C@H](O[C@@H]7C(CO)O[C@H](O[C@@H]8C(CO)O[C@H](O[C@H]1[C@H](O)C2O)C(O)[C@H]8O)C(O)[C@H]7O)C(O)[C@H]6O)C(O)[C@H]5O)C(O)[C@H]4O)C(O)[C@H]3O]

Formula (III)

A ring-shaped molecule made up of eight glucose units
and linked by alpha-1,4 bonds can be referred to as γ-cy-
clodextrin, which is represented by Formula (IV):

Formula (IV)

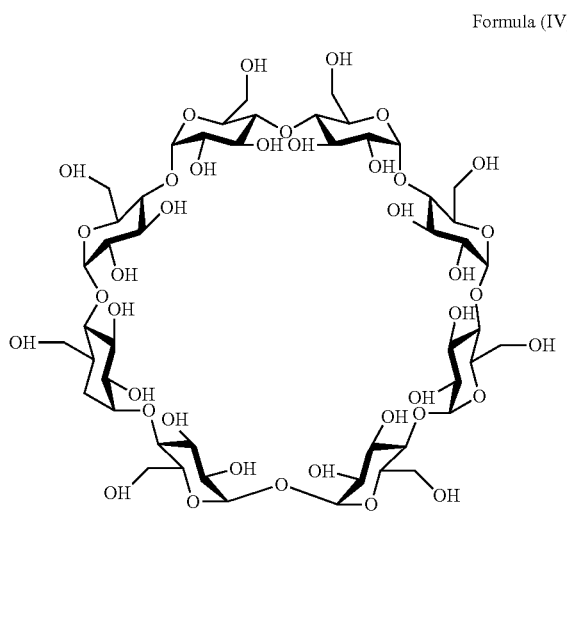 [SMILES: OCC1C[C@H]2O[C@H]3C(CO)O[C@@H](O[C@H]4OC(CO)[C@@H](O[C@H]5OC(CO)[C@@H](O[C@H]6OC(CO)[C@@H](O[C@H]7OC(CO)[C@@H](O[C@H]8C(CO)O[C@@H](O[C@H]9C(CO)O[C@@H](O[C@@H]1C(O)[C@H]2O)[C@H](O)C9O)[C@H](O)C8O)[C@H](O)C7O)[C@H](O)C6O)[C@H](O)C5O)[C@H](O)C4O)[C@H](O)C3O]

Formula (V)

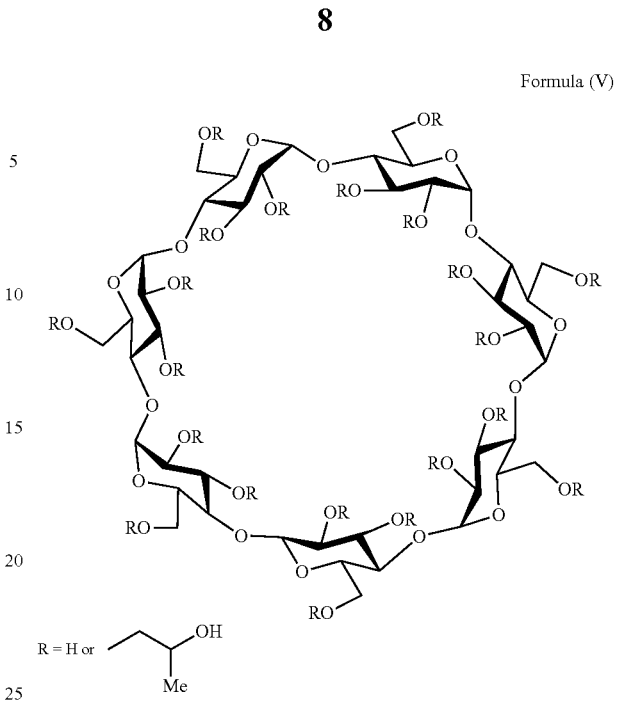

Cyclodextrin can be added to the formulation in the form of cyclodextrin hydrate, for example α-cyclodextrin and γ-cyclodextrin.

Cyclodextrin can be a naturally occurring cyclodextrin or a chemically modified cyclodextrin.

In a preferred embodiment the cyclodextrin of the present invention can be (partially) substituted. Substitution can be achieved with acetyl groups, alkoxy groups such as carboxymethyl, heteroaromatic or aromatic groups, such as benzyl, heteroalkyl or alkyl groups, preferably $C_1$-$C_5$ alkyl groups such as methyl, ethyl, propyl, butyl and pentyl, or with hydroxyalkyl groups, such as hydroxyethyl and hydroxypropyl. Preferably, the cyclodextrins can be (partially) substituted with hydroxypropyl groups.

Examples of cyclodextrins are α-cyclodextrin, β-cyclodextrin, 2-hydroxypropyl-β-cyclodextrin (HPBCD), randomly methylated β-cyclodextrin, sulfobutylether-β-cyclodextrin (SBEBCD), γ-cyclodextrin and 2-hydroxypropyl-γ-cyclodextrin (HPGCD). Preferred are α-cyclodextrin, β-cyclodextrin, 2-hydroxypropyl-β-cyclodextrin (HPBCD) and γ-cyclodextrin.

The term "γ-cyclodextrin" preferably refers to a "non-substituted form" (as shown in above Formula (IV)). This means that the γ-cyclodextrin preferably is not chemically modified, i.e. neither alkylated nor hydroxyl-alkylated.

In a preferred embodiment of the invention the present parenteral formulation comprises β-cyclodextrin as compound (B). More preferably, the β-cyclodextrin can be chemically modified, especially alkylated or hydroxyl-alkylated. Examples of suitable modified β-cyclodextrins are dimethyl β-cyclodextrin, hydroxypropyl β-cyclodextrin, hydroxyethyl β-cyclodextrin, dihydroxypropyl β-cyclodextrin and mixtures thereof.

In a further preferred embodiment hydroxypropylated β-cyclodextrin can be used as compound (B) of the present parenteral formulation, wherein hydroxypropylated β-cyclodextrin is represented by the following Formula (V):

The average degree of substitution of hydroxypropyl β-cyclodextrin preferably varies from 2 to 7.0, more preferably from 3 to 6.5, even more preferably from 4 to 6. In a particularly preferred embodiment the average degree of substitution of hydroxypropyl β-cyclodextrin is about 4.5. In an alternatively particularly preferred embodiment the average degree of substitution of hydroxypropyl β-cyclodextrin is about 5.6. The average degree of substitution is understood as the number of substituents per cyclodextrin ring. Especially an average degree of substitution of 4 to 6 leads to a superior stabilization of the parenteral formulation.

In a preferred embodiment of the invention, the cyclodextrin has a water solubility at 25° C. of from 15 to 1000 mg/ml, preferably 50 to 800 mg/ml and more preferably 100 to 650 mg/ml. The water-solubility can be determined according to the column elution method of the Dangerous Substances Directive (67/548/EEC), Annex V, chapter A6.

The parenteral formulation of the present invention preferably contains cyclodextrin (B) in a concentration of 50 to 300 mg/mL, preferably 65 to 200 mg/mL, more preferably 80 to 150 mg/mL. In a particularly preferred embodiment the parenteral formulation can contain cyclodextrin in a concentration of about 100 mg/mL.

The parenteral formulation of the present invention preferably contains cyclodextrin (B) in an amount of 5 to 30 wt. %, preferably 6.5 to 20 wt. %, more preferably 8.0 to 15.0 wt. %. In a particularly preferred embodiment the parenteral formulation can contain cyclodextrin in an amount of about 10 wt. %.

Cyclodextrin being present in too high concentrations may undesirably dissolve material, for example the plasticizers present in the materials (e.g. bag, syringe, tubing, in-line filter,) when an infusion is administered. Further, too low concentrations of cyclodextrin may not provide sufficient stabilization of the parenteral formulation.

As far as the concentration/amount of cyclodextrin is concerned, the same applies as described above regarding the concentration of siponimod, i.e. the preceding concentrations/amounts apply to a parenteral formulation being present as a concentrate, i.e. in not further diluted form.

Further, the parenteral formulation according to the present invention comprises (C) buffer agent.

A buffer agent is preferably non-toxic, inert and physiologically harmless substance. Buffer agent is added to a liquid formulation to adjust and/or stabilize its pH value. The pH value of the buffer agent ensues after its dissolution in demineralized water. In a preferred embodiment the buffer agent in an amount of 5 mM (0.61 mg/mL), leads to buffered solution having a pH value of 7 to 9.5, preferably 7.2 to 9.3, more preferably 7.5 to 9.0, in particular about 8.0.

Examples of buffer agents are histidine, glycine, arginine, ammonium halides, such as ammonium chloride, triethanolamine (also referred to as tris(2-hydroxyethyl) amine), 2-amino-2-(hydroxymethyl)propan-1,3-diol (also referred to as tris(hydroxymethyl)-aminomethane or trometamol). Preferred are triethanolamine and 2-amino-2-(hydroxymethyl)propan-1,3-diol. Most preferred is 2-amino (hydroxymethyl)propan-1,3-diol.

The parenteral formulation preferably contains buffer agent (C) in a concentration of 0.2 to 2 mg/mL, preferably 0.3 to 1.5 mg/mL, more preferably 0.4 to 1.0 mg/mL, in particular 0.5 to 0.8 mg/L. In a more preferred embodiment the parenteral formulation can contain 2-amino-2-(hydroxymethyl)propan-1,3-diol as buffer agent in a concentration of 0.2 to 2 mg/mL, in particular about 0.6 mg/mL.

The parenteral formulation preferably contains buffer agent (C) in an amount of 0.02 to 0.2 wt. %, preferably 0.03 to 0.15 wt. % mg/mL, more preferably 0.04 to 0.1 wt. %, in particular 0.05 to 0.08 wt. %. In a more preferred embodiment the parenteral formulation can contain 2-amino-2-(hydroxymethyl)propan-1,3-diol as buffer agent in an amount of 0.02 to 0.2 wt. %, in particular about 0.06 wt. %.

As far as the concentration of the buffer agent is concerned, the same applies as described above regarding the concentrations of the further components of the formulation.

Further, the parenteral formulation according to the present invention comprises (D) solvent. As described above, the parenteral formulation can be in liquid form and, thus, suitable for intravenous administration, such as injections or infusions.

Generally, any pharmaceutically acceptable solvent can be used as solvent (D). In a preferred embodiment the solvent is water, in particular water for injection, especially water for injection as defined in Ph.Eur. 8.0, 2014. More specifically, in water for injection the number of colony-building, aerobic germs preferably is not more than 10 microorganisms per 100 mL determined by membrane filtration via the use of agar medium B and at least 200 mL of the water to be tested. Further, the conductivity of the water for injection is at most 1.1 $\mu S \cdot cm^{-1}$ at 20° C. and the total amount of organic carbon is at most 0.5 $mgL^{-1}$.

Further, the parenteral formulation according to the present invention may comprise (E) a tonicity agent.

Generally, "tonicity" can be regarded as the relative concentration of solutes dissolved in solution which determine the direction and extent of diffusion.

Two solutions are considered to be isotonic when their effective osmole concentration is the same as that of another solution. In biology, the solutions on either side of a cell membrane are isotonic if the concentration of solutes outside the cell is equal to the concentration of solutes inside the cell. In this case the cell neither swells nor shrinks because there is no concentration gradient to induce the diffusion of large amounts of water across the cell membrane.

Within the present application a tonicity agent (sometimes also referred to as an isotonicity agent or tonicity adjusting agent) can be referred to as a compound which is added to a formulation, such as a solution, to form a solution showing the same effective osmole concentration as a reference solution. Further, within the present application the reference solution is a body fluid, in particular blood. This means that a tonicity agent is a compound which is used to adjust a solution to be isotonic with a body fluid, in particular blood, such that both solutions exhibit the same osmotic pressure.

A tonicity agent is preferably an inert compound and does not exhibit any pharmacological activity.

Examples of tonicity agents are dextrose monohydrate, anhydrous dextrose, glycerine, mannitol, trehalose dihydrate, potassium chloride and sodium chloride. Sodium chloride, trehalose dihydrate and mannitol are preferred. More preferred are trehalose dihydrate and mannitol, in particular mannitol.

The parenteral formulation preferably contains tonicity agent (E) in a concentration of 5 to 200 mg/mL, preferably 10 to 100 mg/mL, more preferably 20 to 80 mg/mL. In a more preferred embodiment the parenteral formulation can contain trehalose dihydrate as tonicity agent, for example in a concentration of 20 to 100 mg/mL, in particular 60 mg/mL. In a particularly preferred embodiment the parenteral formulation can contain mannitol as tonicity agent, for example in a concentration of 10 to 100 mg/mL, in particular 30 mg/mL.

The parenteral formulation preferably contains tonicity agent (E) in an amount of 0.5 to 20.0 wt. %, preferably 1.0 to 10.0 wt. %, more preferably 2.0 to 8.0 wt. %. In a more preferred embodiment the parenteral formulation can contain trehalose dihydrate as tonicity agent, for example in an amount of 2.0 to 10.0 wt. %, in particular 6.0 wt. %. In a particularly preferred embodiment the parenteral formulation can contain mannitol as tonicity agent, for example in an amount of 1.0 to 10.0 wt. %, in particular 3 wt. %.

As far as the concentration of tonicity agent is concerned, the same applies as described above regarding the concentration of siponimod and/or cyclodextrin, i.e. the preceding concentrations/amounts apply to a parenteral formulation being present as a concentrate, i.e. in not further diluted form.

Generally, all embodiments of the present invention as defined above can be combined with each other. In a preferred embodiment of the invention the parenteral formulation, preferably being in the form of a concentrate, thus comprises (A) siponimod in a concentration of 0.05 to 3.5 mg/mL, preferably of 0.1 to 2.0 mg/mL, more preferably 0.015 to 1.5 mg/mL, in particular 1.0 mg/mL, (B) hydroxypropyl-β-cyclodextrin in a concentration of 50 to 300 mg/mL, preferably of 65 to 200 mg/mL, more preferably 80 to 150 mg/mL, in particular about 100 mg/mL, (C) 2-amino-2-(hydroxymethyl)propan-1,3-diol in a concentration of 0.2 to 2.0 mg/mL, preferably of 0.3 to 1.5 mg/mL, more preferably 0.4 to 1.0 mg/mL, even more preferably 0.5 to 0.8 mg/mL, in particular about 0.60 mg/mL, (D) water; and optionally (E) mannitol in a concentration of 5 to 200 mg/mL, preferably of 10 to 100 mg/mL, more preferably 20 to 80 mg/mL, in particular 30 mg/mL, The present parenteral formulation may further contain one or more pharmaceutically acceptable excipients. Examples of pharmaceutically acceptable excipient(s) are pH-adjusting substances, chelating agents, solubilising agents, thickeners, wetting agents, and antioxidants.

pH-adjusting substances are substances suitable to adjust the pH value of a formulation to a desired value. There are two classes of pH-adjusting substances, the pH-adjusting substances which enhance the pH value of a formulation and the pH-adjusting substances which lower the pH value of a formulation. pH-adjusting substances which enhance the pH value of a formulation can be for example alkaline substances, such as NaOH. pH-adjusting substances which lower the pH value of a formulation can be for example acidic substances such as HCl.

Solubilising agents are agents which help to increase the solubility of the active pharmaceutical ingredient to be more easily dissolved in the desired medium (liquid). The solubilising agents can be broadly classified into surfactants and co-solvents. The surfactants increase the solubility of the drug substances by presenting a lipophilic, whereas co-solvents are defined as a solvent that in conjunction with another solvent (e.g. water) can dissolve a solute. Preferably, the surfactant is selected from polyoxyethylene sorbitanmonooleate (Tween 80), sorbitan monooleate polyoxyethylenesorbitan monolaurate (Tween 20), cremophor EL lecithin, polyoxyethylene-polyoxypropylene copolymers (Pluronics) and mixtures thereof. Preferably, the co-solvent is selected from propylene glycol, glycerin, ethanol, polyethylene glycol (300 and 400), sorbitol, dimethylacetamide, and mixtures thereof.

Preferably, the solubilizing agent is present in the parenteral formulation at a concentration of 0.1 to 5 mg/mL.

Antioxidants are used to prevent/minimize the oxidation reaction of the API or excipients over the shelf life of the product, whereas antimicrobial agents are used to prevent the growth of micro-organisms in the API product. Typical antioxidants are selected from ascorbic acid, acetylcysteine, sulfurous acid salts (bisulfite, metabisulfite), monothioglyercol, citric acid or mixtures thereof.

Preferably, the concentration of antioxidant in the injectable composition is in the range of 0.1 to 5.0 mg/mL.

The parenteral formulation is substantially free from preservatives, which are also referred to in the art as antimicrobial agents. Substantially free means that the amount of preservatives or antimicrobial agents in the injectable composition is below 0.1 mg/mL, preferably below 0.01 mg/mL. In the most preferred embodiment, the injectable composition is free of preservatives.

Typical preservatives or antimicrobial agents which are contained in the compositions of the prior art are selected from e.g. formaldehyde, phenol, meta-cresol, benzyl alcohol, parabens (for example methyl, propyl, butyl), benzalkonium chloride, chlorobutanol, thimerosal, phenylmercuric salts (acetate, borate, nitrate) or mixtures thereof. Propyl, methyl and butyl parabens are referred to chemically as propyl methyl and butyl esters of p-hydroxy benzoic acid. In a preferred aspect, the injectable composition is free from parabens.

The parenteral formulation of the invention is in the form of a lyophilized or alternatively in the form of a liquid. In a preferred embodiment the parenteral formulation is a liquid formulation, i.e. the present formulation is directly prepared as a liquid, preferably a solution, from the above-described ingredients and is stored as liquid without the need of further processing steps. The present parenteral formulation in a form of a liquid formulation is less preferably the result of the steps of (i) freeze-drying (lyophilization), (ii) storing in lyophilized form and (iii) subsequent reconstitution.

Surprisingly it was found that the formulation of the present invention is more stable when stored in liquid form compared to the respective formulations in lyophilized form.

Further, the present application relates to a method for preparing the present parenteral formulation comprising the steps of:
(i) providing components (A) to (D) and optionally (E) a tonicity agent and optionally one or more pharmaceutically acceptable excipients,
(ii) mixing the components of steps (i) to form a solution
(iii) filtering the solution of step (ii).

In step (i) components (A) to (D) and optionally (E) a tonicity agent and optionally one or more pharmaceutically acceptable excipients are provided. In step (i), providing water can preferably include dividing the total amount of water into two parts, wherein one part of the water can be transferred to a suitable reaction vessel. The part of water that can preferably be transferred into the reaction vessel can be at least 60%, preferably at least 70%, in particular about 80% of the total amount of water. The second remaining part of water can be at most 40%, preferably at most 30%, in particular about 20% of the total amount of water.

In step (ii) components of step (i) are mixed. Mixing can for example be carried out by stirring. In a preferred embodiment, components (A) to (D) and optionally (E) a tonicity agent and optionally further pharmaceutical excipients can be added individually in any order to the water in the reaction vessel. In addition, the remaining second part of water can preferably be added to the mixture to adjust the volume of the mixture at a desired target volume. Further, in a preferred embodiment step (ii) is carried out under adjusting the pH value of the solution. It is preferred that a sufficient amount of either NaOH or HCl is added to the mixture to adjust the pH at a desired target value, wherein said target value is preferably a pH of about 8. At the end of step (ii) the mixture is preferably a solution, which can be controlled by visual inspection.

In step (iii) the solution of step (ii) is filtered. Filtering is preferably carried out as microfiltration. A microfiltration is a technique that can remove micron-range particles or biological entities from fluids by passage through a microporous medium, such as a membrane filter. A suitable filter for microfiltration is for example a 0.22µ, polyvinylidene difluoride (PVDF) filter. The filtered solution corresponds to the present parenteral formulation.

In a preferred embodiment the parenteral formulation can be diluted, preferably with 5% glucose or saline, for example in a ratio of 1:4 to 1:1000, preferably 1:10 to 1:100 prior to administration. The diluted formulation is also part of the invention.

The invention is further described by the following non-limiting examples.

EXPERIMENTAL PART

Reference Example: (No Cylclodextrin)

884.2 g trehalose were added to 18000 mL milliQ water and the mixture was stirred until complete dissolution. 12.0 g 2-amino-2-(hydroxymethyl)propan-1,3-diol (Tris, Trometamol) were added and the mixture was stirred until complete dissolution. 100 g polyoxyethylen(20)-sorbitan-monooleat (Tween 80, Polysorbat 80) were added and the mixture was stirred until complete dissolution. 5.56 g (accurately weighted) of siponimod hemifumarate were added and the mixture was stirred until complete dissolution. The pH of the solution was adjusted to a value of 8.0±0.1. MilliQ water was added until a total weight of 20.28 Kg and the mixture was stirred to obtain a homogenous solution. The solution was filtered through a 0.22 µm PVDF filter and the first 5000 mL of the filtrate were discarded. The solution was filled into 6R clear vials (DIN/ISO 8362).

| Composition | Quantity in mg/mL |
|---|---|
| 1-{4-[(1E)-N-{[4-cyclohexyl-3-(trifluoromethyl)benzyl]oxy}ethanimidoyl]-2-ethylbenzyl}-3-azetidinecarboxylic acid/fumaric acid (2:1) co-crystal | 0.278 |
| Trehalosedihydrate | 44.21 |
| Polyoxyethylen(20)-sorbitan-monooleat | 5.0 |
| 2-amino-2-(hydroxymethyl)propan-1,3-diol | 0.6 |
| 1N HCl or 1N NaOH | q.s to pH 8.0 |
| Water | q.s |

The product was lyophilized according to the following cycles
Lyophilization Cycle Parameters
 Lyophilization program for siponimod formulation

| Step | Operation | Time [hh:mm] | Shelf Temperature | Chamber Pressure |
|---|---|---|---|---|
| 1 | Vial loading | As required | 15° | Ambient |
| 2 | Hold | 0:05 | 15° C. | Ambient |
| 3 | Freeze ramp | 00:55 (1.0° C./min) | −40° C. | Ambient |
| 4 | Freeze hold | 2:00 | −40° C. | Ambient |
| 5 | Freeze hold | 1:00 | −40° C. | 0.2 mBar |
| 6 | Freeze ramp | 04:00 (0.083° C./min) | −20° C. | 0.2 mBar |
| 7 | Freeze hold | 80:00 | −20° C. | 0.2 mBar |
| 8 | Freeze ramp | 13:30 (0.025° C./min) | −0° C. | 0.1 mBar |
| 9 | Freeze hold | 10:00 | −0° C. | 0.1 mBar |
| 10 | Secondary drying Rate | 16:30 (0.025° C./min) | 25° C. | 0.1 mBar |
| 11 | Secondary drying hold | 10:00 | 25° C. | 0.1 mBar |
| 12 | Secondary drying hold | 1:00 | 25° C. | 0.1 mBar |
| 13 | Storage | As required/ until vacuum release and stoppering | 15° C. | 0.1 mBar |
| 14 | Stoppering | | 20° C. | 850 ± 50 mbar |

The apparatus used for lyophilisation was "VIRTIS GENESIS 25EL" from SP scientific.
For reconstitution, water for injection was used.
The stability of the product was tested under stress conditions (40° C., 75% rh). After one month the sum of degeneration products was between 10 and 12%.

Example 1: Parenteral Formulation 250 mL milliQ water were transferred into a suitable glass bottle and 50 g hydroxypropyl β-cyclodextrin were added. The mixture was stirred for 30 minutes at 500 rpm and a clear solution was formed. 556 mg (accurately weighted) of 1-{4-[(1E)-N-{[4-cyclohexyl-3-(trifluoromethyl)benzyl]oxy}ethanimidoyl]-2-ethylbenzyl}-3-azetidinecarboxylic acid/fumaric acid (2:1) co-crystal were added and the mixture was stirred for 15 minutes at 500 rpm and a suspension was formed. 305 mg 2-amino-2-(hydroxymethyl)propan-1,3-diol (Tris, Trometamol) were added and the mixture was stirred for 60 minutes at 500 rpm and a clear solution having a pH value of 7.897 was formed. 250 µl of 1N NaOH were added and after stirring for 2 minutes at 500 rpm a clear solution having a pH value of 7.983 was formed. 15 g mannitol were added and the mixture was stirred for 15 minutes at 500 rpm and a clear solution was formed. MilliQ water was added to fill up to a volume of 500 mL of a clear solution having a pH value of 8.015. The solution filtered through a 0.22 µm PVDF filter and the first 20 mL of the filtrate were discarded. The solution was filled into 2R clear vials. The 2 mL clear glass vial and the grey rubber stopper, aluminium flip-off cap nature/nature has been autoclaved at 121° C. for 30 minutes prior to filling. The vials were stored at 2-8° C. until use, each vial containing:

| Composition | Quantity in mg/mL |
|---|---|
| 1-{4-[(1E)-N-{[4-cyclohexyl-3-(trifluoromethyl)benzyl]oxy}ethanimidoyl]-2-ethylbenzyl}-3-azetidinecarboxylic acid/fumaric acid (2:1) co-crystal | 1.112 |
| hydroxypropyl β-cyclodextrin | 100 |
| Mannitol | 30 |
| 2-amino-2-(hydroxymethyl)propan-1,3-diol | 0.61 |
| 1N HCl or 1N NaOH | q.s to pH 8.0 |
| Water | q.s |

Example 2: Parenteral Formulation 250 mL milliQ water were transferred into a suitable glass bottle and 50 g hydroxypropyl β-cyclodextrin were added. The mixture was stirred for 30 minutes at 500 rpm and a clear solution was formed. 556 mg (accurately weighted) of 1-{4-[(1E)-N-{[4-cyclohexyl-3-(trifluoromethyl)benzyl]oxy}ethanimidoyl]-2-ethylbenzyl}-3-azetidinecarboxylic acid/fumaric acid (2:1) co-crystal were added and the mixture was stirred for 15 minutes at 500 rpm and a suspension was formed. 305 mg 2-amino-2-(hydroxymethyl)propan-1,3-diol (Tris, Trometamol) were added and the mixture was stirred for 60 minutes at 500 rpm and a clear solution having a pH value of 7.878 was formed. 250 µl of 1N NaOH were added and after stirring for 2 minutes at 500 rpm a clear solution having a pH value of 7.997 was formed. 3 g sodium chloride were added and the mixture was stirred for 15 minutes at 500 rpm and a clear solution a pH value of 8.112 was formed. 220 µl of 1N HCl were added and after stirring for 10 minutes at 500 rpm a clear solution having a pH value of 8.004 was formed. MilliQ water was added until a volume of 500 mL of a clear solution having a pH value of 8.002 was formed. The solution filtered through a 0.22 µm PVDF filter and the first 20 mL of the filtrate were discarded. The solution was filled into 2R clear vials. The 2 mL clear glass vial and the grey rubber stopper, aluminium flip-off cap nature/nature has been autoclaved at 121° C. for 30 minutes prior to filling. The vials were stored at 2-8° C. until use, each vial containing:

| Composition | Quantity in mg/mL |
|---|---|
| 1-{4-[(1E)-N-{[4-cyclohexyl-3-(trifluoromethyl)benzyl]oxy}ethanimidoyl]-2-ethylbenzyl}-3-azetidinecarboxylic acid/fumaric acid (2:1) co-crystal | 1.112 |
| hydroxypropyl β-cyclodextrin | 100 |
| Sodium chloride | 6 |
| 2-amino-2-(hydroxymethyl)propan-1,3-diol | 0.61 |
| 1N HCl or 1N NaOH | q.s to pH 8.0 |
| Water | q.s |

Example 3: Parenteral Formulation

| Composition | Quantity in mg/mL | Amount per unit vial[4] [mg] (without overfill)[1] |
|---|---|---|
| 1-{4-[(1E)-N-{[4-cyclohexyl-3-(trifluoromethyl)benzyl]oxy}ethanimidoyl]-2-ethylbenzyl}-3-azetidinecarboxylic acid/fumaric acid (2:1) co-crystal | 1.112 | 3.892 |
| hydroxypropyl β-cyclodextrin | 100 | 350.0 |
| Mannitol Pyrogen free | 30 | 105.0 |
| 2-amino-2-(hydroxymethyl)propan-1,3-diol | 0.61 | 2.135 |
| 1N HCl or 1N NaOH | q.s to pH 8.0 | q.s to pH 8.0 |
| Water | q.s | q.s. to 3.5 mL |

[1]This composition refers to the nominal volume of 3.5 mL; the overfill of 0.3 mL is not considered.
[2] 1.112 mg/mL siponimod/fumaric acid co-crystal corresponds to 1 mg/mL of the siponimod free base.
[3] Added as 1N solution
[4]Packaging material: (i) VIAL R 6 ML/20 MM AMBER, (ii) STPF LYO CIIR 20 MM D21-7S/V10-F322-2W/RS (grey rubber stopper), (iii) AR-KAPPE PP/AL 20 MM NATUR/NATUR (aluminum cap with plastic flip-off disk).

Example 4: Stability Tests

4.1. Influence of Different Amounts of Hydroxypropyl-β-Cyclodextrin

A: Solutions (1 mL) containing 1-{4-[(1E)-N-{[4-cyclohexyl-3-(trifluoromethyl)benzyl]oxy}ethanimidoyl]-2-ethylbenzyl}-3-azetidinecarboxylic acid/fumaric acid (2:1) co-crystal (0.556 mg), 0.6 mg 2-amino-2-(hydroxymethyl)propan-1,3-diol (Tris), pH 8, and hydroxypropyl-β-cyclodextrin 100 mg (A1), 150 mg (A2), 200 mg (A3) were prepared.

B: Solutions (1 mL) containing 1-{4-[(1E)-N-{[4-cyclohexyl-3-(trifluoromethyl)benzyl]oxy}ethanimidoyl]-2-ethylbenzyl}-3-azetidinecarboxylic acid/fumaric acid (2:1) co-crystal (0.556 mg), 0.6 mg 2-amino-2-(hydroxymethyl)propan-1,3-diol (Tris), pH 8, and hydroxypropyl-β-cyclodextrin (100 mg, 150 mg, 200 mg) were prepared, lyophilized under the conditions as described in the above Reference Example to form lyophilisates B1, B2 and B3, respectively.

Solutions A1 to A3 and lyophilisates B1 to B3 were stored under stress conditions for one month (1M) and three months (3M). Subsequently the lyophilisates B1 to B3 were reconstituted as described in the above Reference Example and the amounts of impurities of all samples were determined. The amounts of impurities of each sample are shown in the following Table S1:

TABLE S1

|  | A1 | A2 | A3 | B1 | B2 | B3 |
|---|---|---|---|---|---|---|
| 1 M, 40° C., 75% rh | 0.14 | 0.13 | 0.26 | 2.25 | 1.41 | 1.14 |
| 3 M, 40° C., 75% rh | 0.33 | 0.41 | 0.47 | 4.68 | 2.86 | 2.42 |

As can be seen from Table S1, the variants without the lyophilisation exhibit significantly fewer impurities than the ones with lyophilisation.

4.2. Influence of the pH Value

Solutions of the following compositions were prepared:

|  | C1 | C2 | C3 | C4 |
|---|---|---|---|---|
| 1-{4-[(1E)-N-{[4-cyclohexyl-3-(trifluoromethyl)benzyl]oxy}ethanimidoyl]-2-ethylbenzyl}-3-azetidinecarboxylic acid/fumaric acid (2:1) co-crystal | 1.12 mg | 1.12 mg | 1.12 mg | 1.12 mg |
| Hydroxylpropyl β-cyclodextrin | 100 mg | 100 mg | 100 mg | 100 mg |
| Citric acid | 0.961 mg | — | — | — |
| Sodium phosphate monobasic |  | 0.689 mg | 0.689 mg |  |
| 2-amino-2-(hydroxymethyl)-propan-1,3-diol |  |  |  | 0.61 mg |
| 1N HCl or 1N NaOH | q.s pH 5 | q.s pH 6 | q.s pH 7 | q.s pH 8 |
| milliQ water | q.s to 1 mL | q.s to 1 mL | q.s to 1 mL | q.s to 1 mL |

Further, solutions with the compositions of C1 to C4 were prepared and lyophilized under the conditions as described in the above Reference Example to form lyophilisates D1 to D4, respectively.

Solutions C1 to C4 and lyophilisates D1 to D4 were stored under stress conditions for one month (1M) and three months (3M). Subsequently the lyophilisates D1 to D4 were reconstituted as described in the above Reference Example and the amounts of impurities of all samples were determined. The amounts of impurities of each sample were shown in the following Table S2:

TABLE S2

|  | C1 (pH 5) | C2 (pH 6) | C3 (pH 7) | C4 (pH 8) | D1 (pH 5) | D2 (pH 6) | D3 (pH 7) | D4 (pH 8) |
|---|---|---|---|---|---|---|---|---|
| 1 M, 50° C., 75% rh | 0.67 | 0.30 | 0.26 | 0.21 | 4.57 | 2.46 | 1.71 | 3.83 |
| 3 M, 40° C., 75% rh | 0.89 | 0.27 | 0.24 | 0.19 | 4.57 | 2.46 | 1.69 | 3.72 |

As can be seen from Table S2, the variants without the lyophilisation exhibit significantly fewer impurities than the ones with lyophilisation. Further, with regard to the pH value, it turned out that the variants without lyophilisation are advantageously stabilized at a pH of 8, while the optimum of stabilization for the lyophilized variants is a pH of 7.

Example 5: Crystallization

Crystalline Form A of 1-{4-[(1E)-N-{[4-cyclohexyl-3-(trifluoromethyl)benzyl]oxy}ethanimidoyl]-2-ethylbenzyl}-3-azetidinecarboxylic acid/fumaric acid (34.6 mg) was dissolved in 5 ml of acetone at 50° C. and the resultant clear colourless solution was directly stored in the fridge. After one day of storage the white precipitate was filtered over a P4 glass filter and air was sucked through the sample for about 3 minutes.

Crystal Structure of Siponimod-Fumaric Acid Modification A

TABLE 5.1

Crystal data and structure refinement

| Parameter | Result |
|---|---|
| Compound | Siponimod-fumaric acid [propanol/H2O] |
| Empirical formula | $C_{31} H_{37} F_3 N_2 O_5$ |
| Formula weight | 574.63 |
| Temperature | 100(2) K |
| Wavelength | 1.54178 Å |
| Crystal system | Triclinic |
| Space group | P-1 |
| Unit cell dimensions | a = 17.586(8) Å    α = 102.37(2)° |
|  | b = 19.320(8) Å    β = 96.48(3)° |
|  | c = 25.912(11) Å   γ = 90.00(3)° |
| Volume | 8542(6) Å$^3$ |
| Z | 12 |
| Density (calculated) | 1.340 g/cm$^3$ |
| Absorption coefficient | 0.867 mm$^{-1}$ |
| F(000) | 3648 |
| Crystal size | 0.24 × 0.15 × 0.06 mm$^3$ |
| Theta range for data collection | 2.53 to 68.33° |
| Index ranges | −20 <= h <= 20, −23 <= k <= 23, −31 <= l <= 31 |
| Reflections collected | 29946 |
| Independent reflections | 29946 [R(int) = 0.0000] |
| Completeness to theta = 68.33° | 95.5% |
| Absorption correction | Semi-empirical from equivalents |
| Max. and min. transmission | 0.9498 and 0.8189 |
| Refinement method | Full-matrix least-squares on F$^2$ |
| Data/restraints/parameters | 29946/1476/2234 |
| Goodness-of-fit on F$^2$ | 1.023 |
| Final R indices [I > 2sigma(I)] | R1 = 0.0748, wR2 = 0.2147 |
|  | R1 = 0.1013, wR2 = 0.2377 |
| Largest diff. peak and hole | 0.722 and −0.870e · Å$^{-3}$ |

Intensity data were collected at 100 K on a Bruker AXS three-circle diffractometer with monochromated Cu(K$_a$)-radiation (Helios MX confocal mirror monochromator), microfocus rotating anode generator, and a Smart 6000 CCD detector using the SMART software (Bruker AXS (2005)). 13 w-scans at different f-positions were performed to ensure appropriate data redundancy. Data processing and global cell refinement were performed with Saint (Bruker AXS (2006)). A semi-empirical absorption correction was applied, based on the intensities of symmetry-related reflections measured at different angular settings (Sheldrick G M (2008)).

TABLE 5.2

Hydrogen bonds for siponimod-fumaric acid in angstrom (Å) and degree

| D-H . . . A | d(D-H) | d(H . . . A) | d(D . . . A) | <(DHA) |
|---|---|---|---|---|
| N(31)—H(31) . . . O(156)#3 | 0.93 | 1.72 | 2.646(6) | 176.0 |
| N(31)—H(31) . . . O(157)#3 | 0.93 | 2.60 | 3.183(6) | 121.1 |
| N(71)—H(71) . . . O(36) | 0.93 | 1.71 | 2.632(6) | 171.6 |
| N(71)—H(71) . . . O(37) | 0.93 | 2.61 | 3.190(6) | 121.2 |
| N(111)—H(111) . . . O(196) | 0.93 | 1.76 | 2.692(5) | 174.6 |
| N(111)—H(111) . . . O(197) | 0.93 | 2.63 | 3.191(5) | 119.3 |
| N(151)—H(151) . . . O(76)#4 | 0.93 | 1.72 | 2.645(6) | 175.5 |
| N(151)—H(151) . . . O(77)#4 | 0.93 | 2.61 | 3.199(6) | 121.4 |
| N(191)—H(191) . . . O(236)#3 | 0.93 | 1.77 | 2.694(5) | 175.3 |
| N(191)—H(191) . . . O(237)#3 | 0.93 | 2.62 | 3.184(5) | 119.3 |
| N(231)—H(231) . . . O(116)#4 | 0.93 | 1.76 | 2.686(5) | 171.5 |
| N(231)—H(231) . . . O(117)#4 | 0.93 | 2.65 | 3.205(5) | 119.1 |
| O(301)—H(301) . . . O(37) | 0.84 | 1.70 | 2.512(5) | 163.3 |
| O(308)—H(308) . . . O(157)#5 | 0.84 | 1.70 | 2.512(5) | 163.2 |
| O(311)—H(311) . . . O(237) | 0.84 | 1.70 | 2.502(5) | 159.7 |
| O(316)—H(316) . . . O(117)#6 | 0.84 | 1.71 | 2.504(5) | 156.7 |
| O(317)—H(317) . . . O(77) | 0.84 | 1.71 | 2.517(5) | 160.7 |
| O(321)—H(321) . . . O(197) | 0.84 | 1.69 | 2.504(5) | 161.6 |

Symmetry transformations used to generate equivalent atoms:
1 −x + 1, −y + 3, −z + 2
2 −x + 1, −y, −z
3 −x + 2, −y + 1, −z + 1
4 −x + 1, −y + 1, −z + 1
5 x, y + 2, z + 1
6 x + 1, y + 1, z + 1

The four pairs (O—H . . . O), which are presented in the table above and listed below, show that the bond length between the protons and the carboxylic acid oxygen of fumaric acid is only half of the distance to the carboxylic acid oxygen of siponimod, proving that the proton sits firmly on the fumaric acid, hence, making siponimod-fumaric acid a co-crystal.

The four pairs (O—H . . . O):
(a): O(301)-H(301) . . . O(37), (b): O(311)-H(311) . . . O(237), (c): O(317)-H(3317) . . . O(77) and (d): O(321)-H (321) . . . O(197).

The invention claimed is:

1. A liquid parenteral formulation, comprising: (A) siponimod, (B) cyclodextrin, (C) buffer agent and (D) solvent.

2. The liquid parenteral formulation according to claim 1, further comprising (E) a tonicity agent.

3. The liquid parenteral formulation according to claim 1 wherein the formulation comprises containing siponimod (A) in a concentration of 0.05 mg/ml to 3.5 mg/ml.

4. The liquid parenteral formulation according to claim 1, wherein cyclodextrin (B) is hydroxypropyl-p-cyclodextrin.

5. The liquid parenteral formulation according to claim 1, wherein the formulation comprises containing cyclodextrin (B) in a concentration of 50 mg/ml to 300 mg/ml.

6. The liquid parenteral formulation according to claim 2, wherein the tonicity agent (E) is mannitol.

7. The liquid parenteral formulation according to claim 2, wherein the formulation comprises containing the tonicity agent (E) in a concentration of 5 mg/ml to 200 mg/ml.

8. The liquid parenteral formulation according to claim 1, wherein a buffered solution having a pH value of 7.0 to 9.5 is obtainable by dissolving the buffer agent (C) in an amount of 0.005 M in 1000 ml (5 mM) of demineralized water at 23° C.

9. The liquid parenteral formulation according to claim 1, wherein the buffer agent (C) is 2-amino-2-(hydroxymethyl) propan-1,3-diol.

10. The liquid parenteral formulation according to claim 1, wherein the formulation comprises containing buffer agent (C) in a concentration of 0.2 mg/ml to 2.0 mg/ml.

11. The liquid parenteral formulation according to claim 1, wherein the formulation comprises containing: (A) siponimod in a concentration of 0.05 mg/ml to 3.5 mg/ml, (B) hydroxypropyl-β-cyclodextrin in a concentration of 50 mg/ml to 300 mg/ml, (C) 2-amino-2-(hydroxymethyl)propan-1,3-diol in a concentration of 0.2 mg/ml to 2.0 mg/ml, (D) water, and (E) mannitol in a concentration of 5 mg/ml to 200 mg/ml.

12. The liquid parenteral formulation according to claim 1, wherein the parenteral formulation has not been freeze-dried and reconstituted.

13. A diluted liquid parenteral formulation, wherein the diluted formulation comprises comprising a parenteral formulation according to claim 1 and a diluting agent.

14. The diluted liquid parenteral formulation, comprising a parenteral formulation according to claim 13 and a diluting agent, wherein the diluting agent preferably is 5% glucose.

15. A method for preparing a liquid parenteral formulation according to claim 1, wherein the method comprises comprising the steps of: (i) providing components (A) to (D), and optionally (E) a tonicity agent, and optionally one or more pharmaceutically acceptable excipients, (ii) mixing the components of steps (i) to form a solution, and (iii) filtering the solution of step (ii).

16. The method according to claim 15, wherein step (ii) is carried out under adjusting the pH value of the solution.

17. The diluted liquid parenteral formulation according to claim 13, wherein the diluting agent is saline.

* * * * *